United States Patent
Futagawa et al.

Patent Number: 5,827,233
Date of Patent: Oct. 27, 1998

[54] PREFILLED SYRINGE

[75] Inventors: Hitoshi Futagawa, Kusatsu; Mitsuo Murakami, Amagasaki; Masafumi Aramata, Neyagawa; Toshikazu Hirayama, Ohtsu; Yohji Arifuku, Kusatsu, all of Japan

[73] Assignee: Nissno Corporation, Osaka-fu, Japan

[21] Appl. No.: 772,530

[22] Filed: Dec. 24, 1996

[30] Foreign Application Priority Data

Dec. 26, 1995 [JP] Japan .................................. 7-338448

[51] Int. Cl.⁶ ...................................................... A61M 5/00
[52] U.S. Cl. ............................................ 604/232; 604/218
[58] Field of Search ................................... 604/232, 264, 604/271, 272, 218, 187

[56] References Cited

U.S. PATENT DOCUMENTS

| 1,388,946 | 8/1921 | Goold . |
| 2,514,575 | 7/1950 | Hein et al. . |
| 5,453,093 | 9/1995 | Haining .................................. 604/110 |

FOREIGN PATENT DOCUMENTS

| 0047398A1 | 3/1982 | European Pat. Off. . |
| 0090413A | 10/1983 | European Pat. Off. . |
| 2826241 | 12/1979 | Germany . |
| 55-32602 | 8/1980 | Japan . |
| 534669 | 9/1993 | Japan . |
| 1103917 | 2/1968 | United Kingdom . |
| 1230543 | 5/1971 | United Kingdom . |

*Primary Examiner*—John D. Yasko
*Attorney, Agent, or Firm*—Birch, Stewart, Kolasch & Birch, LLP

[57] ABSTRACT

A prefilled syringe comprises a barrel (1) having at a distal end a needle-connecting portion (11) and at the proximal end an open end; a plastic tubular container (3) having a mouth (31) and a flexible hollow cylindrical body (32) and containing a liquid medicament (S) previously charged therein, and a plunger (2) inserted into the barrel (1) through the open end thereof and slidably held therein. The tubular container (3) is held in the barrel (1) so that the mouth (31) thereof is placed in a lumen of the needle-connecting portion (11) of the barrel (1) and that the cylindrical body (32) is peeled off from the inner wall of the barrel (1) and squeezed into a space between the barrel (1) and plunger (2) when the plunger (2) is pushed into the barrel.

10 Claims, 8 Drawing Sheets

PREFILLED SYRINGE

BACKGROUND OF THE INVENTION

1. Field of the Invention

The present invention relates to a prefilled syringe and, more particularly, to a pre-filled syringe which is substantially free from elution of any lubricant such as silicone oil, and which is small in sliding resistance between a syringe barrel and a plunger to be reciprocated within a bore of the barrel.

2. Description of the Prior Art

There have been known prefilled syringes, i.e., syringes of which a barrel is previously filled with a liquid medicament and which is so designed as to administer the liquid medicament by fitting a hypodermic needle over a tip of the barrel after removing a hermetic seal from the tip of the barrel. In such a prefilled syringe, the barrel filled with a liquid medicament is generally sealed at one end by a rubber gasket and at the other end or a needle-connecting portion by a rubber plate. The needle-connecting portion is covered and sealed by a cap fitted thereon to ensure the sterility of the contents.

However, such prefilled syringes of the prior art have a serious problem for use in infusion since additives such as sulfur, vulcanization accelerators or impurities elute in the liquid medicament from the rubber plates or rubber gaskets used as the sealing members during storage of the syringes.

The above problem of the prefilled syringe of the prior art may be solved by use of a syringe, proposed in examined Japanese Utility model publication No. 55-32602, comprising a barrel made of glass and a sealing member of which surfaces to be contacted with a liquid medicament are coated or covered with a thin film of a plastic material other than fluoroplastics. However, such a syringe has a problem that the resin coated sealing member does not slide smoothly since the barrel is made of glass. Although this problem can be overcome by use of a sealing member or gasket coated with or made of fluoroplastics since fluoroplastics have a good sliding property, such sealing members or gaskets are poor in liquid-tightness and airtightness when combined with the glass barrels.

For the above reasons, disposable syringes widely used today are those employing a barrel made of plastics. When the plastic barrel is combined with a gasket made of plastics other than fluoroplastics, it is required to apply a lubricant such as silicone oils on sliding surfaces of the gasket since increase in liquid-tightness and airtightness between the gasket and barrel causes decrease in slidability of the gasket. However, silicone oil is a foreign substance for the medicament to be administered and causes contamination of the medicament due to elution of fine particles.

To solve such problems, it has been proposed in examined Japanese utility model publication No. 5-34669 to use a gasket of which all the surfaces to be in contact with a liquid medicament and to be slid on the inner wall of the barrel are covered with a thin film of a plastic material selected from the group consisting of polytetrafluoroethylene, ethylenetetrafluoroethylene copolymer and very high polymeric polyethylene and which has a length of a contacting surface between a peripheral portion of the gasket and the inner wall of the barrel being limited within a certain range.

Although the gaskets disclosed in examined publication No. 5-34669 provide no problem when used for the ordinary syringes, they causes problems in liquid-tightness and airtightness when used for prefilled syringes. For example, if the plunger is pressed hard during storage, the liquid medicament may leak out from the syringe different from the close contact between the elastic gasket and barrel.

SUMMARY OF THE INVENTION

It is therefore an object of the present invention to provide a prefilled syringe which overcomes the aforesaid disadvantages, which is substantially free from contamination of the medicament or from elution of foreign substances from parts, which has good liquid-tightness and airtightness, and which is small in sliding resistance between the plunger and a barrel in use.

According to the present invention, the above and other objects are solved by providing a prefilled syringe including a flexible tubular container which has been previously filled with a liquid medicament and, when performing administration, adapted to be folded up and squeezed into a space between the plunger and barrel by a plunger.

According to the present invention, there is provided a prefilled syringe comprising a barrel having at a distal end with a needle-connecting portion or a tip for needle attachment, and at the proximal end an open end; a plastic tubular container composed of a flexible hollow cylindrical body having a mouth at one end and containing a liquid medicament previously charged therein, said tubular container being held in said barrel so that the mouth thereof is placed in a lumen of said needle-connecting portion of the barrel; and a plunger inserted into said barrel through the open end thereof and slidably held therein, the cylindrical body of said plastic tubular container being adapted to be folded up and squeezed into a space between the barrel and plunger when the plunger is forced into the barrel.

In order to make mixed administration of medicaments possible, the prefilled syringe may be so constructed that other liquid medicament can be sucked into the tubular container by pulling the plunger and then pushed out therefrom together with the previously charged liquid medicament through a needle by pushing the plunger. This may be done, for example, by fixing the mouth of the tubular container to the needle-connecting portion of the barrel and fixing the bottom of the tubular container to the distal end of the plunger. To this end, the tubular container may be provided at its mouth with an annular rib which engages with an annular groove or recess formed in an inner wall of the needle-connecting portion of the barrel. The tubular container may be provided at the central part of its bottom with an engaging recess or projection, while the plunger may be provided at the central part of the top thereof with an engaging projection or recess which can be engaged with the engaging recess or projection of the tubular container.

In order to allow the body of the tubular container to be folded up and squeezed into a space between the barrel and plunger when forcing the plunger into the barrel, the plunger is so formed as to have a diameter smaller than an inner diameter of the barrel to form a space between the plunger and barrel. The plunger is provided with longitudinal ribs on an outer wall thereof so that the sliding axis of the plunger coincides with the longitudinal axis of the barrel. The longitudinal ribs extend from the proximal end of the plunger toward the distal end thereof by a certain length and are brought into sliding contact with the inner wall of the barrel. Preferably, the longitudinal ribs terminate at a middle part of the plunger to form a cylindrical space between the plunger and the barrel at the distal portions thereof. Alternatively, the barrel may be provided with an auxiliary tubular member having an outer diameter equal to the inner diameter of the barrel and an inner diameter slightly larger than the outer diameter of the plunger, the auxiliary tubular member being centered on the axis of the barrel so that the sliding axis of the plunger coincides with the longitudinal axis of the barrel.

The tip or needle-connecting portion of the syringe may be constituted by a tubular connecting means extending axially and outwardly from the distal end of the barrel, and a separate needle-connecting member connected to the tubular connecting means. In this case, it is necessary to seal a gap formed between the mouth of the tubular container and the needle-connecting member by providing a packing between them.

The needle-connecting portion may be covered with a cap or sealed with a thin plastic film to prevent the tubular container from leaking of the liquid medicament charged therein.

According to the present invention, the needle-connecting portion may be provided on the tip of the tubular container. Thus, there is provided a prefilled syringe comprising: a barrel having at a distal end a narrowed opening and at the proximal end an open end; a tubular container of plastics including a flexible tubular body and a needle-connecting portion and being previously filled with a liquid medicament, said tubular container being held in said barrel so that the needle-connecting portion is extruded by a certain length from the narrowed opening of the barrel; and a plunger inserted into said barrel through the open end thereof and slidably held therein, said cylindrical body of the plastic tubular container being adapted to be folded up and squeezed into a space between the barrel and plunger when the plunger is forced into the barrel. The needle-connecting portion may be sealed with a cap or a thin film in the same manner as that in the first form of the prefilled syringe mentioned above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects, features and advantages of the present invention will become apparent from the following detailed description on preferred embodiments thereof with reference to the accompanying drawings in which.

DETAILED DESCRIPTION OF THE PREFERRED EMBODIMENTS

Figure 1:
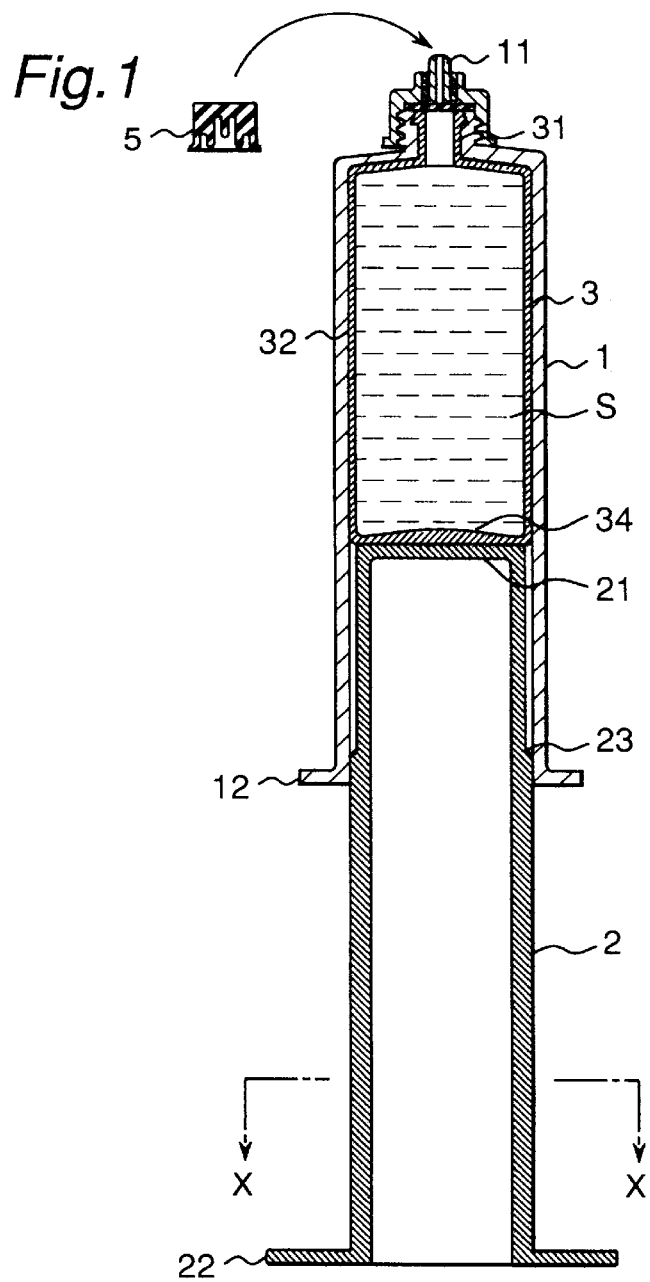
FIG. 1 is a cross-sectional view of a first form of a prefilled syringe according to the present invention with a cap being removed.
Figure 2:
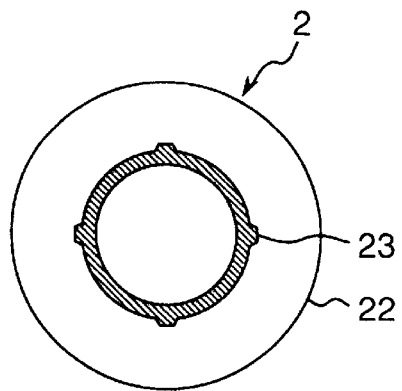
FIG. 2 is a cross-sectional view of the prefilled syringe taken along a line X—X in FIG. 1.

The present invention will be explained on the first embodiment thereof. Referring now to FIGS. 1 to 6, there is shown a first form of a prefilled syringe according to the present invention, which comprises a barrel 1 having at a distal end a needle-connecting portion 11 and at the proximal end an open end; a plastic tubular container 3 including a mouth 31 and a flexible body 32 and being previously filled with a liquid medicament S, the tubular container 3 being held in the barrel 1 so that the mouth 31 thereof is fitted in a lumen of the needle-connecting portion 11 of the barrel 1; and a plunger 2 inserted into the barrel 1 through the open end thereof and slidably held within the bore of the barrel 1, the cylindrical body 32 of the plastic tubular container 3 being adapted to be folded up and squeezed into a space between the barrel 1 and plunger 2 when pushing the plunger 2 into the barrel 1.

The barrel 1 is a cylindrical member made of a transparent plastic material such as polypropylene, polyethylene, cyclopolyolefine, methylpentene resin (TPX polymer), polycarbonate, acrylic resin, polyvinyl chloride, polystyrene, acrylonitrile-butadiene-styrene copolymer (ABS) or the like.

Figure 5:
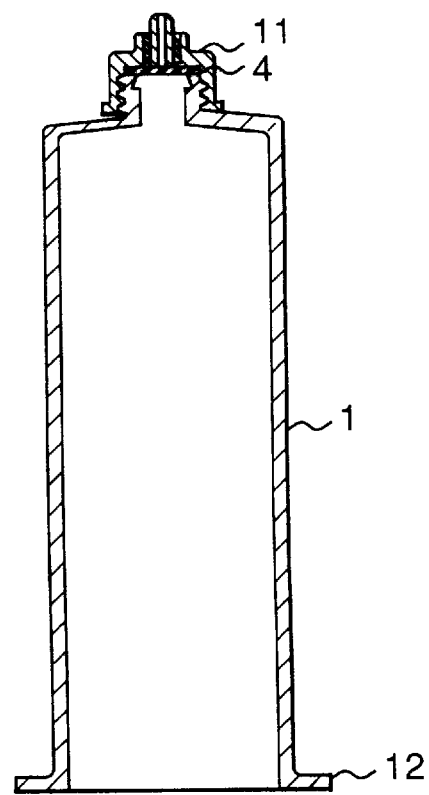
FIG. 5 is a cross-sectional view of a barrel used in the prefilled syringe of FIG. 1.

As illustrated in FIGS. 1 and 5, a syringe barrel 1 has a configuration narrowed at a distal end in the same manner as the general hypodermic syringe to form a tip or hollow needle-connecting portion 11 over which a hub of an unillustrated syringe needle is fitted. The proximal end of the barrel 1 is opened and generally provided with flanges 12 for gripping the syringe with fingers.

Figure 6:
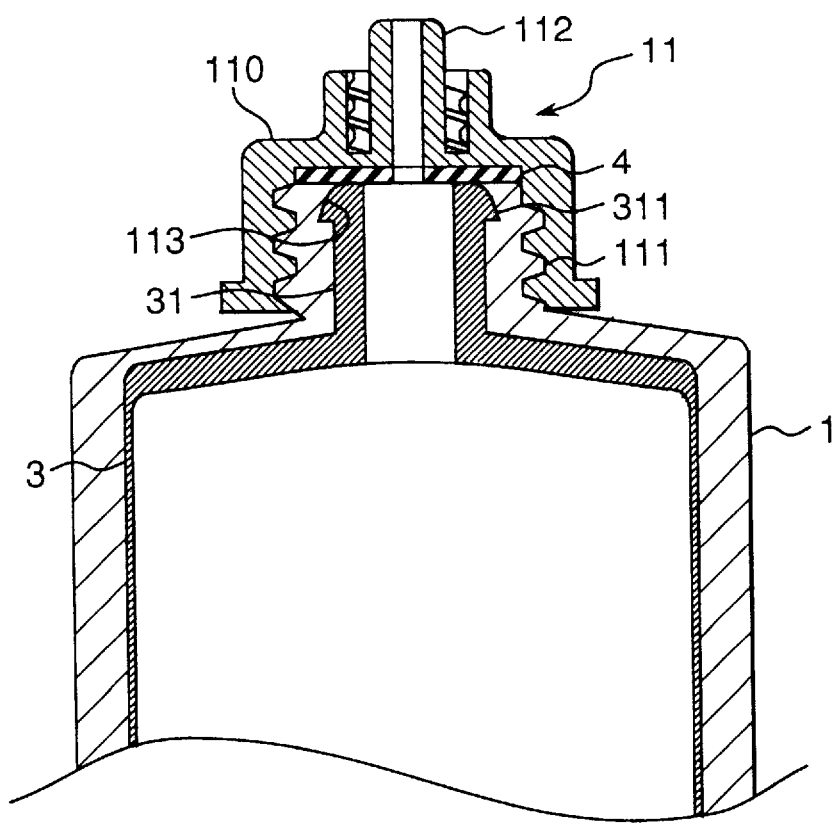
FIG. 6 is an enlarged cross-sectional view of a needle-connecting portion of the prefilled syringe of FIG. 1.
Figure 7A:
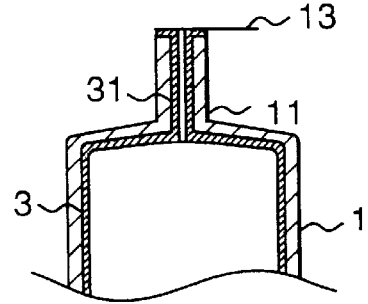
FIGS. 7A and 7B are cross-sectional views illustrating modified forms of a needle-connecting portion of the prefilled syringe according to the present invention.
Figure 7B:
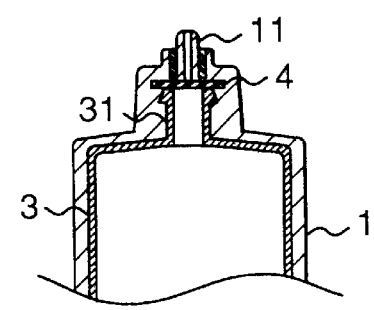
Figure 8:
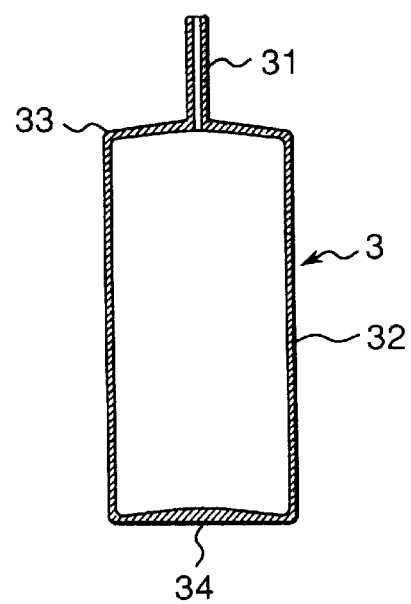
FIG. 8 is a cross-sectional view illustrating another form of a tubular container used in the prefilled syringe according to the present invention.
Figure 9:
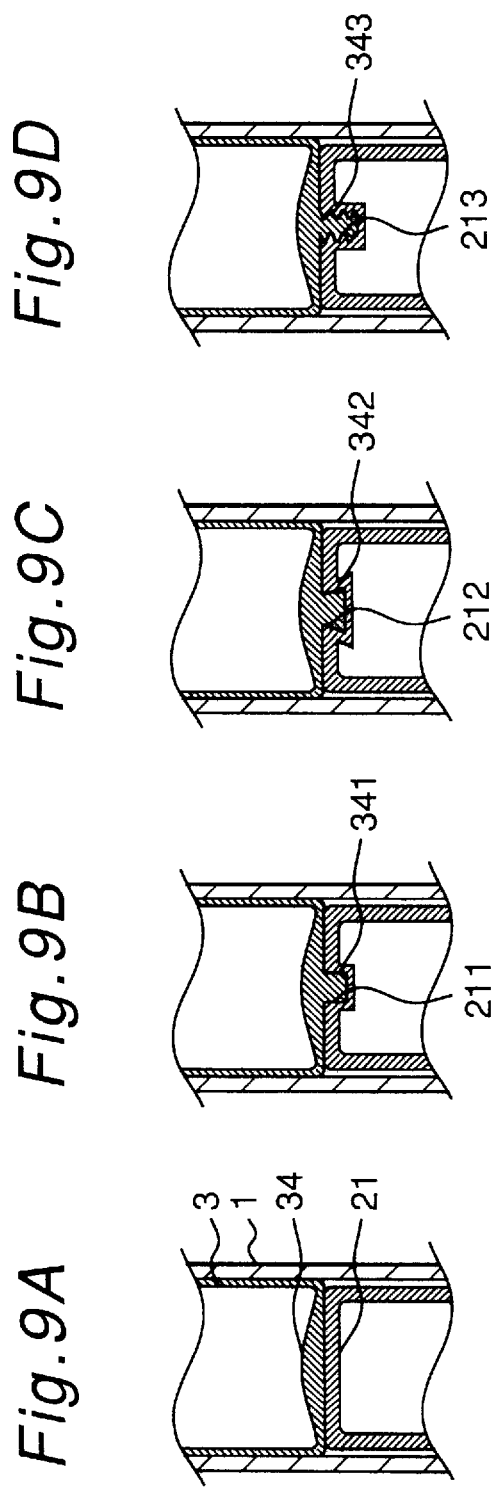
FIGS. 9A–9D are cross-sectional views illustrating various forms of a combination of a tubular container with a plunger.

As illustrated in detail in FIG. 6, the needle-connecting portion 11 is formed separate from the barrel 1 as a luer tip member 110 engaged with an engaging means 111 such as male thread formed in the outer wall of the narrowed distal end. The luer tip member 110 is generally formed from polypropylene, polyethylene or the like and has a luer tip 112 extending upwardly from the top thereof and centered on the axis of the tubular container 3. In this case, it is necessary to seal the gap between the mouth 31 of the tubular container 3 and the luer tip member 110 with a packing 4. In this embodiment, the needle-connecting portion 11 is formed as a separate member in the above embodiment, but this needle-connecting portion 11 may be integrally molded with the barrel 1 as shown in FIG. 7B.

The needle-connecting portion 11 may be covered with a cap 5 made of butyl rubber, isoprene rubber, polyethylene or the like to prevent the leakage of the liquid medicament charged in the container 3. Alternately, the needle-connecting portion 11 may be sealed at its opening with a thin film 13 of polyethylene or polypropylene by thermal adhesion, as shown in FIG. 7A.

The tubular container 3 previously filled with a liquid medicament S is inserted into the barrel 1 through its open end and held therein. The needle-connecting portion 11 is covered with a cap 5.

As illustrated in FIGS. 1, 4, 8–10, the tubular container 3 is a bag-like body having a mouth 31 and a flexible body 32 and at least the latter is formed from a thermoplastic resin such as polypropylene, polyethylene, poly-1-butene, thermoplastic elastomer, ethylene-vinyl acetate copolymer (EVA) or the like in the form of a film. The tubular container 3 is fitted in the bore of the barrel 1 so that the mouth 31 is fitted in the lumen of the needle-connecting portion 11. The body 32 of the tubular container 3 is so designed as to have an outer diameter equal to or slightly larger than the inner diameter of the barrel 1 when the tubular container 3 not being held in the bore of the barrel 1, so that the body 32 can be in close contact with the inner surface of the barrel 1 when the tubular container 3 filled with a liquid medicament S is held in the barrel 2. The mouth 31, an abutment shoulder 33 and a bottom of the tubular container 3 are formed into a relatively thick form to give a suitable rigidity.

The mouth 31 is preferably fixed to the needle-connecting portion 11 to prevent it from movement when the plunger 2 is pulled backward. This may be done, for example, by engagement of an annular rib 311 provided on the mouth 31 and an annular groove 113 or recess (not illustrated) provided in the inner wall of the needle-connecting portion 11 as shown in FIG. 6. Alternatively, the mouth 31 may be fixed by thermal deformation of a top portion of a mouth having a length longer than that of the hollow needle-connecting means 111 of the barrel 1 so as to pass through the tip of the needle-connecting means 111 when put in the barrel 1, with an unillustrated mould heated to a softening point of the container material, as shown in FIG. 7A.

The bottom 34 of the tubular container 3 is generally in close contact with the top 21 of the plunger 2. The bottom 34 of the tubular container 3 and the top 21 of the plunger 2 may be engaged with any contacting means as shown in FIGS. 9A–9D. In FIG. 9A, the bottom 34 is formed into a flat surface together with the top 21 of the plunger 2. In FIGS. 9B and 9C, the bottom 34 is provided with a projection 341 or 342 in the form of a disk or inverted frustum of a cone, which is engaged with a recess 211 or 212 formed in the top wall of the plunger 2. In FIG. 9D, the bottom 34 is provided with a male threaded projection 343 engaged with a female threaded recess 213 formed in the top of the plunger 2. In the embodiments illustrated in FIGS. 9C and 9D, if the mouth 31 of the tubular container 3 is fixed to the lumen of needle-connecting portion 11, it is possible to suck in a liquid medicament into the tubular container 3 by pulling the plunger 2, thus making it possible to mix the liquid medicament with another liquid medicament.

Figure 3:
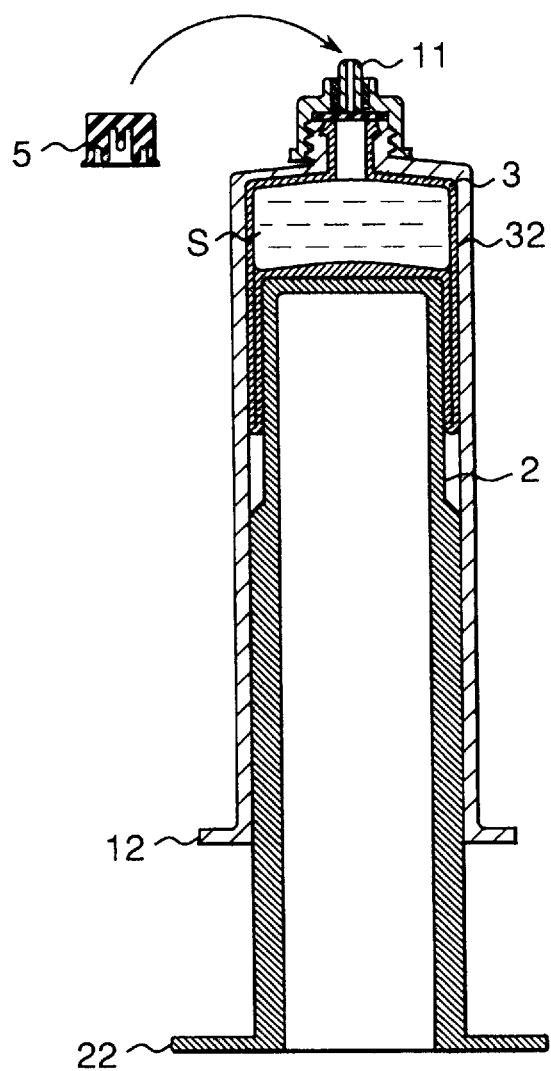
FIG. 3 is a cross-sectional view of the prefilled syringe of FIG. 1, showing the state that a plunger is moved to a middle position of a barrel.
Figure 4:
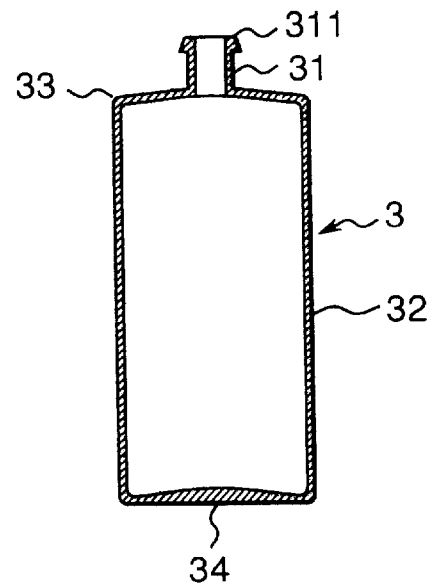
FIG. 4 is a cross-sectional view of a tubular container used in the prefilled syringe of FIG. 1.

The container body 32 is formed from plastic resin such as polypropylene, polyethylene, poly-l-butene in a form of film and is physically stuck on the inner wall of the barrel 1. Thus, if the plunger 2 is designed so as to have an outer diameter D smaller than the inner diameter of the barrel 1 or if the plunger 2 is so formed that the sum of the outer diameter of the plunger and double thickness of the container body 32 is smaller than the inner diameter of the barrel 1 at the least, the container body 32 would be peeled off little by little from the inner wall of the barrel 1 when forcing the plunger into the barrel 1 and the peeled portion of the container body 32 would be folded up and put into a space between the barrel and plunger as illustrated in FIG. 3.

The plunger 2 is generally formed into a cylindrical member with a synthetic resin such as polypropylene, polyethylene, polycarbonate or the like and inserted into the barrel 1 with the tubular container 3 being held therein through the open end of the barrel 1. The plunger 2 is generally formed into a hollow cylindrical member closed at a top 21 and provided with two or more (e.g. four in this embodiment) longitudinal ribs 23 to center it on the longitudinal axis of the barrel or to allow the plunger to be slidingly moved in the direction parallel to the longitudinal axis of the barrel 1. At the proximal end, the plunger is provided with a flange 22 to make it easy to perform pushing operation. Though the longitudinal ribs 23 are generally provided so that they are symmetrical with respect to the axis of the plunger 2, it is preferred to provide three or four longitudinal ribs 23.

Figure 10:
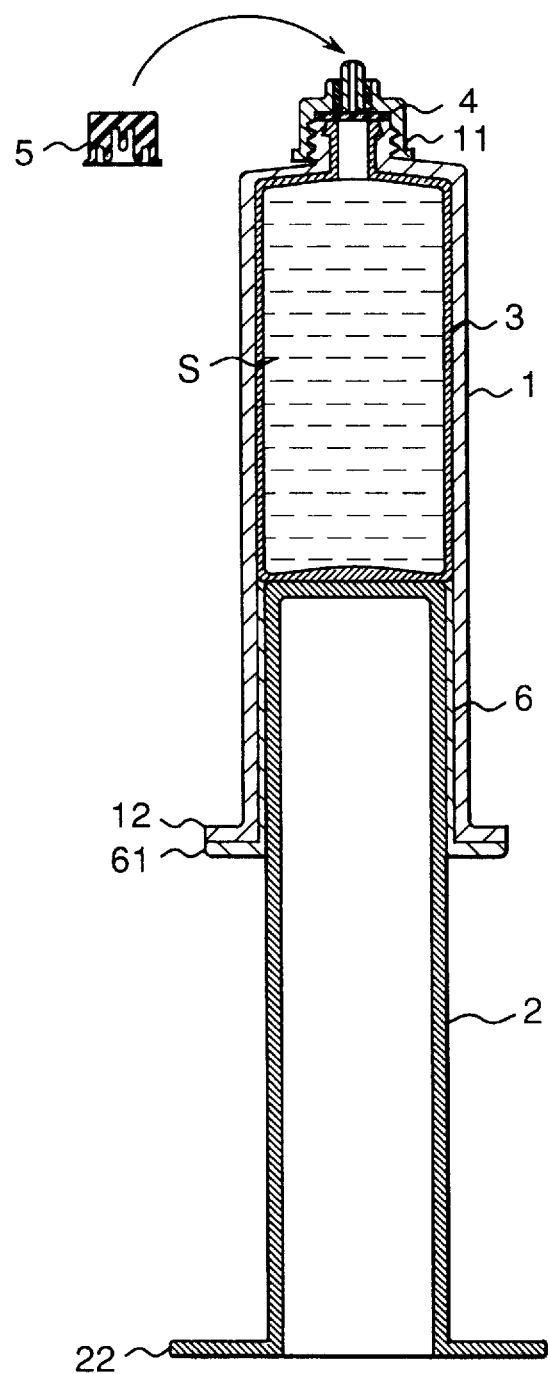
FIG. 10 is a longitudinal cross-sectional view illustrating a modification of the first form of the prefilled syringe according to the present invention with a cap being removed.

As previously mentioned, the tip 21 of the plunger 2 is formed into a configuration illustrated in FIGS. 9A–9D. The plunger 2 may be centered on the axis of the barrel 1, for example, as shown in FIG. 10, by employing a cylindrical auxiliary member or adapter 6 which has an outer diameter substantially equal to the inner diameter of the barrel 1, an inner diameter slightly larger than the outer diameter of the plunger 2, and a length substantially equal to a difference between the length of the barrel 1 and the length of the container 3. This adapter 6 is inserted into the bore of the barrel 1 and held therein by friction fit, while the plunger 2 is slidably put in the lumen of the adapter 6.

In this embodiment, the adapter 6 is provided at its rear end with a flange 61 to be engaged with the flange 12 of the barrel 1 to put it in place, but this may be done by modification of the barrel 6 instead of provision of the flange 61. For example, the barrel is modified so as to have a stepped bore (not illustrated in the drawings) of which a rear part is being slightly enlarged in diameter as compared with the diameter of the front part. In this case, the adapter is seated on the stepped portion between the front and rear parts of the bore and prevented from further movement into the bore.

Further, the plunger may be provided with an O-ring to control the sliding resistance between the plunger and the barrel. The O-ring may be made of any elastic material including natural rubber or synthetic rubber since the O-ring and plunger are never brought into contact with the liquid medicament in the tubular container.

The needle-connecting portion may be provided on the tip of the tubular container 3. The second embodiment of the present invention is a prefilled syringe having a needle-connecting portion 301 provided at the tip of the tubular container 30.

Figure 11:
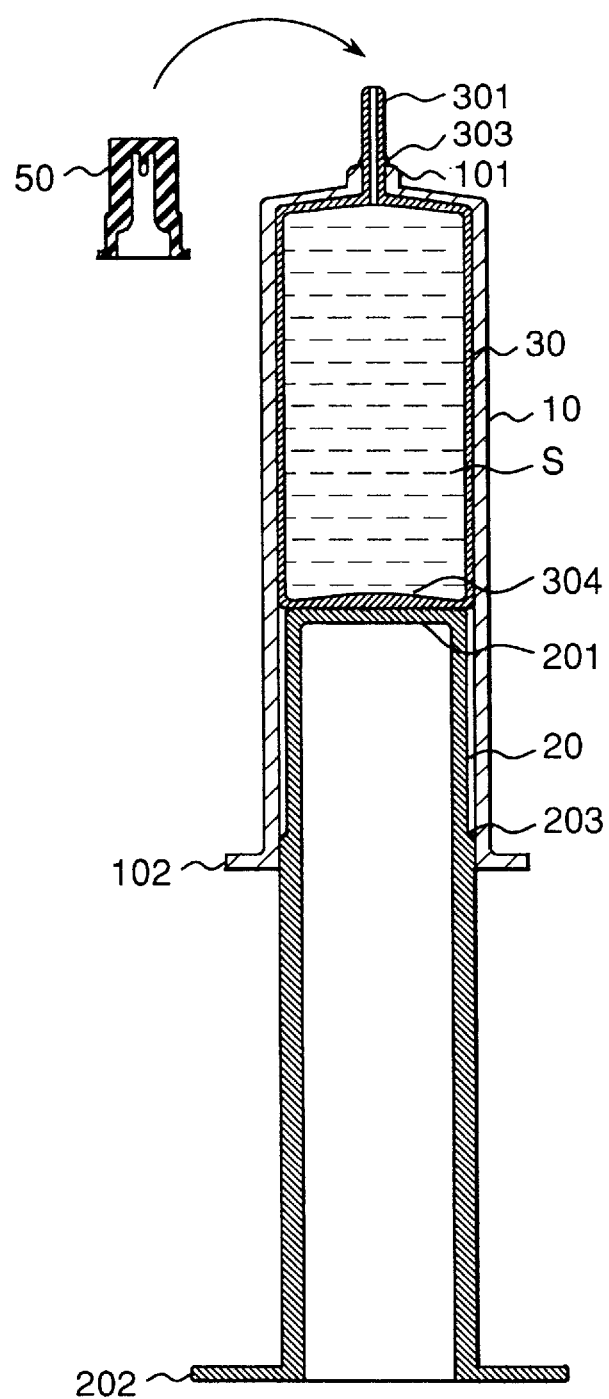
FIG. 11 is a longitudinal cross-sectional view of a second form of a prefilled syringe according to the present invention with a cap being removed.

As illustrated in FIG. 11, the needle-connecting portion 301 is not provided on the narrowed end of the barrel 10, but is constituted by the mouth of the tubular container 30. The needle-connecting portion 301 has a configuration so that a conventional hypodermic needle may be coupled to the syringe. Preferably, the needle-connecting portion 301 is engaged with the barrel 10, thereby allowing other medicament to be sucked into the tubular container 30 through the bore of the tip 301 by pulling a plunger 20 within the bore of the barrel 10. The fitting of the needle-connecting portion 301 of the tubular container 30 to the barrel 10 may be performed by providing an annular rib 303 on the needle-connecting portion 301. This annular rib 303 is forced into the bore of the neck portion of the barrel 10 and engaged with the narrowed open end 101 of the barrel 10 when the tubular container 30 is inserted into the barrel 10. In this embodiment, the tip of the needle-connecting member 301 is protected by fitting a cap 50 thereon in the same manner as that of the prefilled syringe shown in FIGS. 1 and 10, but it may be carried out by sealing it with a thin plastic film.

In FIG. 11, reference numeral 102 indicates a flange of the barrel 10, 202 indicates a flange of the plunger 20, and 203 indicates longitudinal ribs. The configurations of the plunger 20, combination of a top 201 of the plunger 20 and the and a bottom 304 of the tubular container 30 are the same with those of the first form of the prefilled syringes according to the present invention, except for the shape of the narrowed end of the barrel 10, and the needle-connecting portion including a mouth and a neck portion of the tubular container 30. Thus, there would be no need to explain the details of these portions.

EXAMPLES 1–3

Using polypropylene as a molding material for barrels and plungers and polyethylene as a molding material for tubular containers, there were respectively prepared 100 units of prefilled syringes having a configuration shown in FIG. 1 and having a capacity of 10, 20 or 50 ml. The plunger was so designed as to have a diameter smaller than the inner diameter of the corresponding barrel by 0.3 mm, and centered on the axis of the barrel by four longitudinal ribs which are provided on the outer surface and which are symmetrical with respect to the axis. These ribs extend axially from the proximal end toward the distal end of the plunger but terminate at positions short of the distal end to form a cylindrical space of 0.3 mm between the barrel and plunger. The tubular containers were 0.1 mm in thickness of the container body 32 and were charged with distilled water to determine a sliding resistance between the plunger and the barrel and the number of fine particles with a particle size of not less than 0.5 $\mu$m eluted into the distilled water (Japanese pharmaceutical code defines that the number of fine particles with a particle size of not less than 0.5 $\mu$m must be not more than 100). The results are listed in Table 1 along with the results for prefilled syringes prepared in the following comparative examples.

COMPARATIVE EXAMPLES 1–3

Using polypropylene as a molding material for barrels and plungers and butyl rubber as a material for gaskets, there were respectively prepared 10 units of prefilled syringes of the prior art having a capacity of 10, 20 or 50 ml and composed of a barrel and a plunger, the open end being sealed with a gasket of butyl rubber. The measurements were made in the same manner as in the above examples on the sliding resistance between the plunger and the barrel and the number of fine particles with a particle size of not less than 0.5 $\mu$m eluted into the distilled water.

TABLE 1

|  | Sliding resistance (kg) | Number of Particles (particles/ml) |
| --- | --- | --- |
| Ex. 1 | 0.05 | 6 |
| Ex. 2 | 0.08 | 4 |
| Ex. 3 | 0.12 | 3 |
| Comp. Ex. 1 | 0.15 | 55 |
| Comp. Ex. 2 | 0.35 | 41 |
| Comp. Ex. 3 | 1.08 | 28 |

As can be seen from the results shown in Table 1, the prefilled syringe according to the present invention have the following advantages:

(1) It is substantially free from contamination of a liquid medicament due to elution of a lubricating oil since the prefilled syringe having a gasketless structure which does not need any lubricant such as silicone oil.

(2) The liquid medicament can be pushed out from the tubular container with a very small force since the resistance which occurs at the time of pushing operation of the plunger is a sum of a resistance caused by peeling off the tubular container from the barrel and a sliding resistance between the tubular container and the barrel.

(3) It is possible to store the liquid medicament in the prefilled syringe for a long period since the liquid medicament is charged into the tubular container and hermetically sealed, and since the thin walled tubular container is held in the barrel and closed therein.

(4) There is no need to perform segregated disposal since this prefilled syringe employs no parts made of glass.

(5) The liquid medicament can be administered in sterilized conditions as the prefilled syringe constitutes a closed system.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A prefilled syringe comprising:

a barrel having a narrowed distal end and an open proximal end, said narrowed distal end having an annular groove in an inner wall thereof, said narrowed distal end further having engaging means formed in an outer wall thereof;

a plunger inserted into said barrel through the open end thereof and slidably held therein, said plunger having a diameter smaller than an inner diameter of the barrel to form a cylindrical space between said plunger and said barrel;

a tubular container having a mouth at one end and containing a liquid medicament charged therein, said mouth having an annular rib at a distal end thereof, said tubular container being held in said barrel and fixed to said barrel with the mouth of the container inserted into a lumen of said narrowed distal end and with said annular rib engaged with said annular groove in the narrowed distal end of the barrel, said tubular container being adapted to be folded up and squeezed into the cylindrical space between the plunger and the barrel when forcing the plunger into said barrel;

a luer tip member having a luer tip and being engaged with said engaging means formed on the outer wall of the narrowed distal end of the barrel; and sealing means located between the mouth of said tubular container and the luer tip member for sealing a gap between the mouth of said tubular member and said luer tip member.

2. The prefilled syringe according to claim 1, wherein the tubular container is fixed at a closed bottom thereof to one end of the plunger.

3. The prefilled syringe according to claim 1, wherein said tubular container has an engaging recess or projection provided at a closed bottom thereof for engagement with one end of the plunger.

4. The prefilled syringe according to claim 1, wherein said tubular container is made of plastic.

5. The prefilled syringe according to claim 1, wherein the annular groove has a diameter larger than a diameter of said inner wall of said narrowed distal end of said barrel.

6. The prefilled syringe according to claim 1, wherein said annular rib has a diameter larger than an outer diameter of said mouth of said tubular container.

7. The prefilled syringe according to claim 1, wherein the sealing means is a plastic film.

8. The prefilled syringe according to claim 1, further including a cap for covering said distal end of said barrel.

9. The prefilled syringe according to claim 1, wherein the plunger is provided at its outer wall with longitudinal ribs so that the sliding axis of the plunger coincides with the longitudinal axis of the barrel, said longitudinal ribs extending from the proximal end of the plunger toward the distal end thereof by a certain length and being in sliding contact with the inner wall of the barrel.

10. The prefilled syringe according to claim 1, wherein the barrel is provided with an auxiliary tubular member having an outer diameter equal to the inner diameter of the barrel and an inner diameter slightly larger than the outer diameter of the plunger, the auxiliary tubular member being centered on the axis of the barrel so that the sliding axis of the plunger coincides with the longitudinal axis of the barrel.

* * * * *

UNITED STATES PATENT AND TRADEMARK OFFICE
CERTIFICATE OF CORRECTION

PATENT NO. : 5,827,233
DATED : October 27, 1998
INVENTOR(S) : Futagawa, et. al.

It is certified that error appears in the above-indentified patent and that said Letters Patent is hereby corrected as shown below:

Title page, item [73], Assignee: should read --Nissho Corporation --.

Signed and Sealed this

Sixteenth Day of November, 1999

Attest:

Attesting Officer

Q. TODD DICKINSON

Acting Commissioner of Patents and Trademarks